(12) United States Patent
Keuenhof

(10) Patent No.: US 8,310,407 B2
(45) Date of Patent: Nov. 13, 2012

(54) EMERGENCY PROVISION WHEN USING A LARGE DISPLAY

(75) Inventor: Bernd Keuenhof, Kleinsendelbach (DE)

(73) Assignee: Siemens Aktiengesellschaft, Munich (DE)

( * ) Notice: Subject to any disclaimer, the term of this patent is extended or adjusted under 35 U.S.C. 154(b) by 753 days.

(21) Appl. No.: 12/272,371

(22) Filed: Nov. 17, 2008

(65) Prior Publication Data

US 2009/0135093 A1  May 28, 2009

(30) Foreign Application Priority Data

Nov. 23, 2007  (DE) .......................... 10 2007 056 420

(51) Int. Cl.
  *G09G 3/04*  (2006.01)
(52) U.S. Cl. .......................................... 345/1.2; 345/2.2
(58) Field of Classification Search .................... 345/1.1, 345/1.3, 2.2
  See application file for complete search history.

(56) References Cited

U.S. PATENT DOCUMENTS

| | | | |
|---|---|---|---|
| 6,696,980 B1 * | 2/2004 | Langner et al. | 340/971 |
| 7,190,390 B2 * | 3/2007 | Hett et al. | 348/58 |
| 7,250,922 B2 * | 7/2007 | Sakaniwa | 345/1.3 |
| 7,567,233 B2 * | 7/2009 | Garibaldi et al. | 345/157 |

FOREIGN PATENT DOCUMENTS

| | | |
|---|---|---|
| DE | 601 03 156 T2 | 5/2005 |
| EP | 1 299 784 B1 | 9/2005 |

OTHER PUBLICATIONS

German Office Action dated Oct. 13, 2008 with English translation.
Bonfiglio et al., "10.4: New Display Solutions for the Image-Centric Era of Healthcare," SID Symposium Digest of Technical Papers, May 2007, vol. 38, Issue 1, pp. 123-126 (2007).

* cited by examiner

*Primary Examiner* — Kevin M Nguyen
*Assistant Examiner* — Sepideh Ghafari
(74) *Attorney, Agent, or Firm* — Lempia Summerfield Katz LLC

(57) ABSTRACT

A large display is provided for the representation of medical images. The large display comprises at least a first and a second zone which can be controlled and operated independently of each other. Furthermore, an image configuration is provided which describes the representation on the large display during normal operation. Also provided is an emergency image configuration which describes the representation in the second zone of the large display in the event of failure or fault of the representation in the first zone. In the event of a fault, provision is made for switching over to an emergency operating mode in which the representation in the second zone is determined by the emergency configuration. The present embodiments have the advantage of providing protection against a failure of the large display, failure of which would disrupt medical operation.

14 Claims, 4 Drawing Sheets

FIG 1

| Live Sub A | Live Nat Ref A | Ref 2 A |
|---|---|---|
| Live SUB B | Live Nat Ref B | Ref 2 B |
| ECG Data | System Control ||

Biplane Configuration 1
Neuro: with Live Sub, Live Nat/Ref, Ref 2

FIG 2

| Live Sub A | Ref 2 A | Syngo Workplace |
|---|---|---|
| Live SUB B | Ref 2 B | ECG |
| System Control || Taskbar |

Biplane Configuration 2
Neuro: with Live Sub, Ref 2, Syngo Workplace, ECG

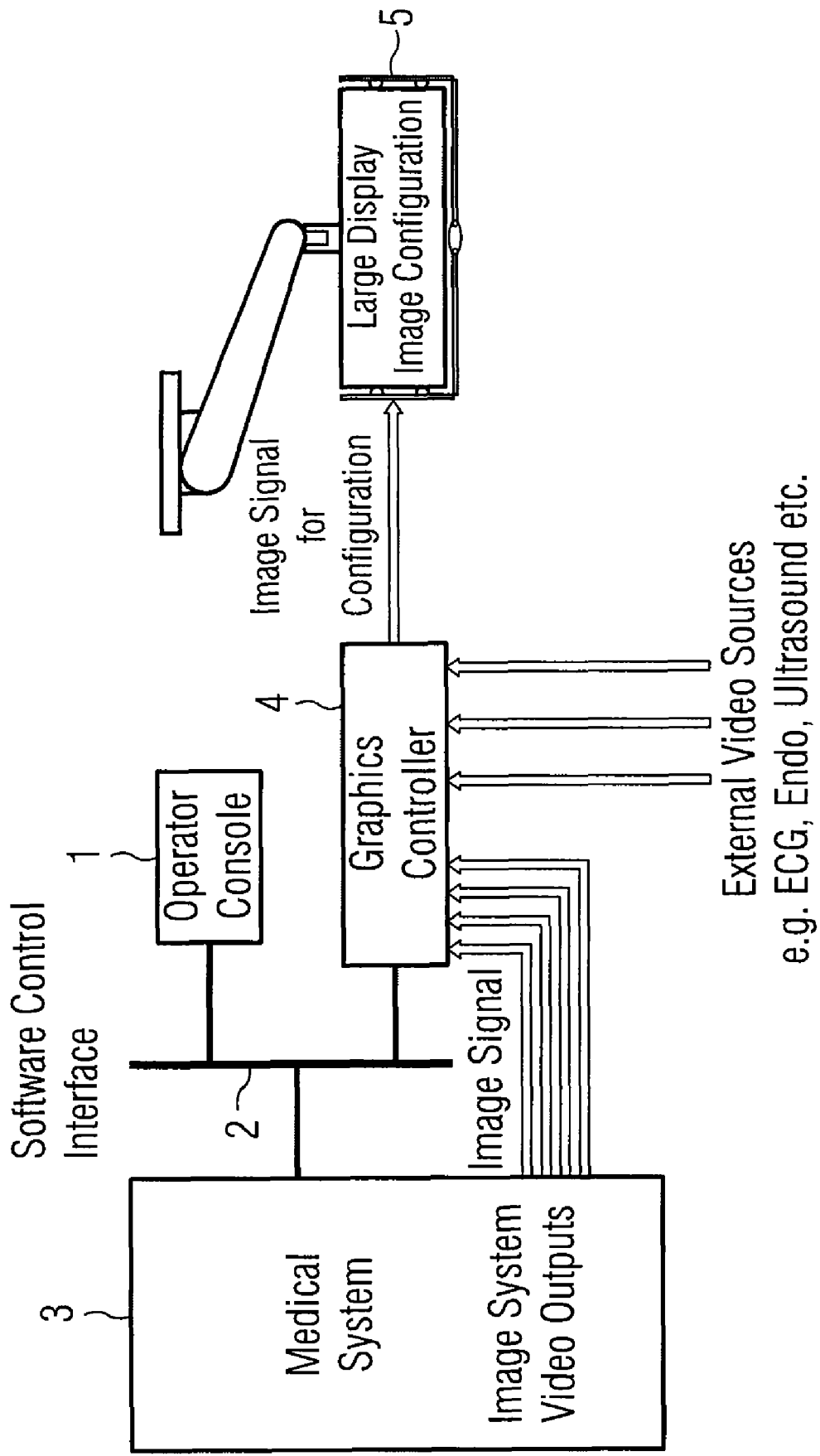

EMERGENCY PROVISION WHEN USING A LARGE DISPLAY

This patent document claims the benefit of DE 10 2007 056 420.3 filed Nov. 23, 2007, which is hereby incorporated by reference.

BACKGROUND

The present embodiments relate to a large display for the representation of medical images and to a medical display system.

In the context of medical examinations in hospitals, a plurality of representations or images are used to register the body part under examination. A plurality of different perspectives can be represented, for example, by a medical imaging method. Various imaging methods or modalities (e.g. X-ray, computed tomography, ultrasound, magnetic resonance tomography, video, scattering of laser beams, etc.) are also combined to obtain as much information as possible concerning medical conditions in a patient. A plurality of displayed images are used when images that are recorded under different conditions (e.g. before and after administration of contrast agents) are superimposed. The plurality of displayed images are used to obtain a representation having maximum contrast (difference method).

During a medical examination, different medical images are represented on individual dedicated image playback devices. Accordingly, a separate image playback device is required for each video (graphics card) output interface of a medical imaging system. For example, in X-ray system examination workstations, eight or even more image playback devices are currently required in the examination room, including color displays for electrocardiogram (ECG) and ultrasound.

A solution including a multiplicity of displays is confusing, inflexible, and not easily scalable. The publication "New Display Solutions for the Image-Centric Era of Healthcare" by S. Bonfiglio and L. Albani in SID Symposium Digest of Technical Papers—May 2007—Volume 38, Issue 1, pp. 123-126 discloses a plurality of medical images being represented on a large display in order to get by with one display per examination workstation. The publication describes an input device by which images that must be output on a large display can be selected from a multiplicity of possible medical images. The input device (tablet PC) has a visual output that includes a first zone including selectable images and a second zone showing the images that are represented on the large display. By moving an image from the first zone into the second zone, the image is selected and its representation on the large display is changed.

The use of a large display has greater risks in the event of a failure. In the case of representation on separate monitors, the simultaneous failure of a plurality of monitors due to a defect is very improbable, and therefore the majority of the images usually remain available. Specifically in the case of medical interventions it is of primary importance that faults do not cause the intervention to be interrupted or even abandoned. The use of a large display is critical insofar as the failure of the now sole display would mean that there are no longer any images available which enable the examination or treatment to be continued.

SUMMARY AND DESCRIPTION

The present embodiments may obviate one or more of the drawbacks inherent in the related art. For example, in one embodiment, a large display may be used to protect against faults in the context of medical applications.

In one embodiment, a large display is provided to represent medical images. The display includes at least two zones that can be controlled and operated independently of each other. A fault relating to one zone does not affect the other zone. The inputs and power supplies or electronic parts of the two zones are implemented separately or redundantly.

The large display or large screen may be an image playback device, a display, a monitor, or a visual output which, with respect to its technical properties (e.g., resolution, luminosity and dimensions), allows the simultaneous output of at least two images or image streams of sufficient size and quality for diagnostic or therapeutic applications in hospitals. The large display may be, for example, a monitor having a resolution of 4 megapixels to more than 8 megapixels and a screen size of 30" to 64". The monitor may be suitable for use as a large display in a hospital.

An image configuration, which describes the representation on the large display, may be used during normal operation. According to this representation, an overall image includes image elements (e.g., individual images and information to be represented) during normal operation. An emergency image configuration may describe the representation in one zone of the large display in the event of a failure or fault relating to the representation in the other zone. The emergency configuration may include elements that are represented in the failed zone during normal operation. Provision is made for switching over to an emergency operating mode in which the representation in the second zone is determined by the emergency configuration.

The switching over can be done manually using an input unit. Alternatively, an automatic switchover may be used. Automatic switchover may include sending verification messages to the large display or to various mutually independent parts of the large display. Alternatively, independent parts of the large display regularly send status reports to a verification unit. The absence of status reports may trigger the switchover.

In one embodiment, the orderly execution of medical examinations and treatments are protected against failures and faults. An emergency configuration may be defined for each separately controllable (e.g. via separate cable connections) and operable zone of the large display. An emergency image configuration, which represents the image information that is required for the examination or treatment, may be specified in an area that is reduced in size (e.g., due to the failure). Accordingly, in the event of a fault, the physician may continue working immediately after switching over to the emergency image configuration.

The large display may be an element of a medical display system. The medical display system may include an adapting apparatus for composing an overall image in accordance with an image configuration for the representation on the large display. The adapting apparatus may represent (e.g., display or illustrate) the overall image on the large display. The adapting apparatus may have access to an emergency image configuration and may compose the image in accordance with the emergency configuration following a switchover to emergency operating mode. The display system may include an input unit via which a switchover to emergency operating mode can be effected. In one embodiment, the input unit allows the specification of image configurations and emergency image configurations.

BRIEF DESCRIPTION OF THE DRAWINGS

FIG. 1 illustrates a first image configuration;
FIG. 2 illustrate a second image configuration;

FIG. 5 illustrates a medical visual output system.

DETAILED DESCRIPTION

FIG. 1 shows an image configuration in which six images (e.g., Live Sub A, Live Sub B, Live Nat Ref A, Live Nat Ref B, Ref 2 A, and Ref 2 B) are represented (displayed) on the large display. The images Live Sub A and Live Sub B are subtraction images. The images Live Nat Ref A and Live Nat Ref B are unprocessed recordings. The images Ref 2 A and Ref 2 B are reference images.

The combination of images shown in FIG. 1 may be used in an angiography examination, for example. In an angiography examination, vessels are examined by X-ray recordings. Accordingly, a radioactive contrast agent is introduced into the vessels and an X-ray recording is made. A good contrast can be obtained by eliminating the background of the recording by an X-ray recording taken before the contrast agent is used such that only the vessels can still be seen (e.g., a difference image). This therefore requires a recording before administration of the contrast agent (e.g., Ref 2 A and Ref 2 B), on which recording is superimposed on the recording after administration of the contrast agent (e.g., Live Nat Ref A and Live Nat Ref B) for the purpose of eliminating the background, in order to generate a difference recording (e.g., Live Sub A and Live Sub B) in which essentially only the vessels are represented.

The image configuration may include a strip at the bottom edge of the large display. Electrocardiogram (ECG) data and system control information may be shown in the strip at the bottom edge. The image configuration shown in FIG. 2 differs in that the two images on the right-hand side of FIG. 1 have been moved into the center and system-related information (e.g., Syngo Workplace) and ECG data are included or output instead.

Figure 3:
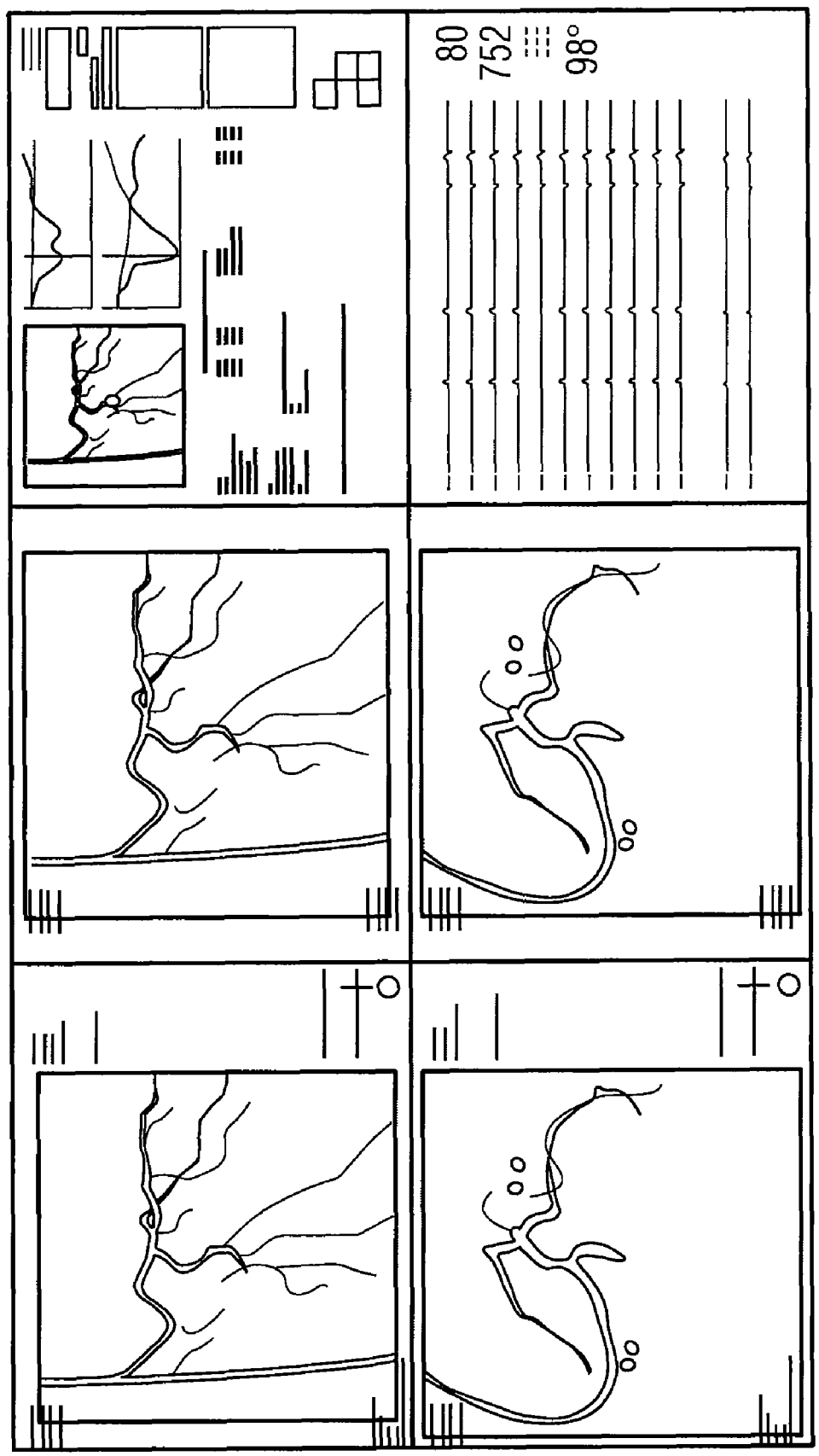
FIG. 3 illustrates a representation on a large display.

FIG. 3 shows a representation of an image configuration on a large display. On the left-hand side are four images which show angiographic recordings of vessels. Information that is relevant for the workflow, for example, ECG curves, is output on the right-hand side. The large display includes two halves, an upper half and a lower half, which can be controlled and operated separately. If one of the two halves fails, an emergency image can be represented on the other half by an emergency configuration. This takes place, for example, by an input interface as shown in FIG. 4.

Figure 4:
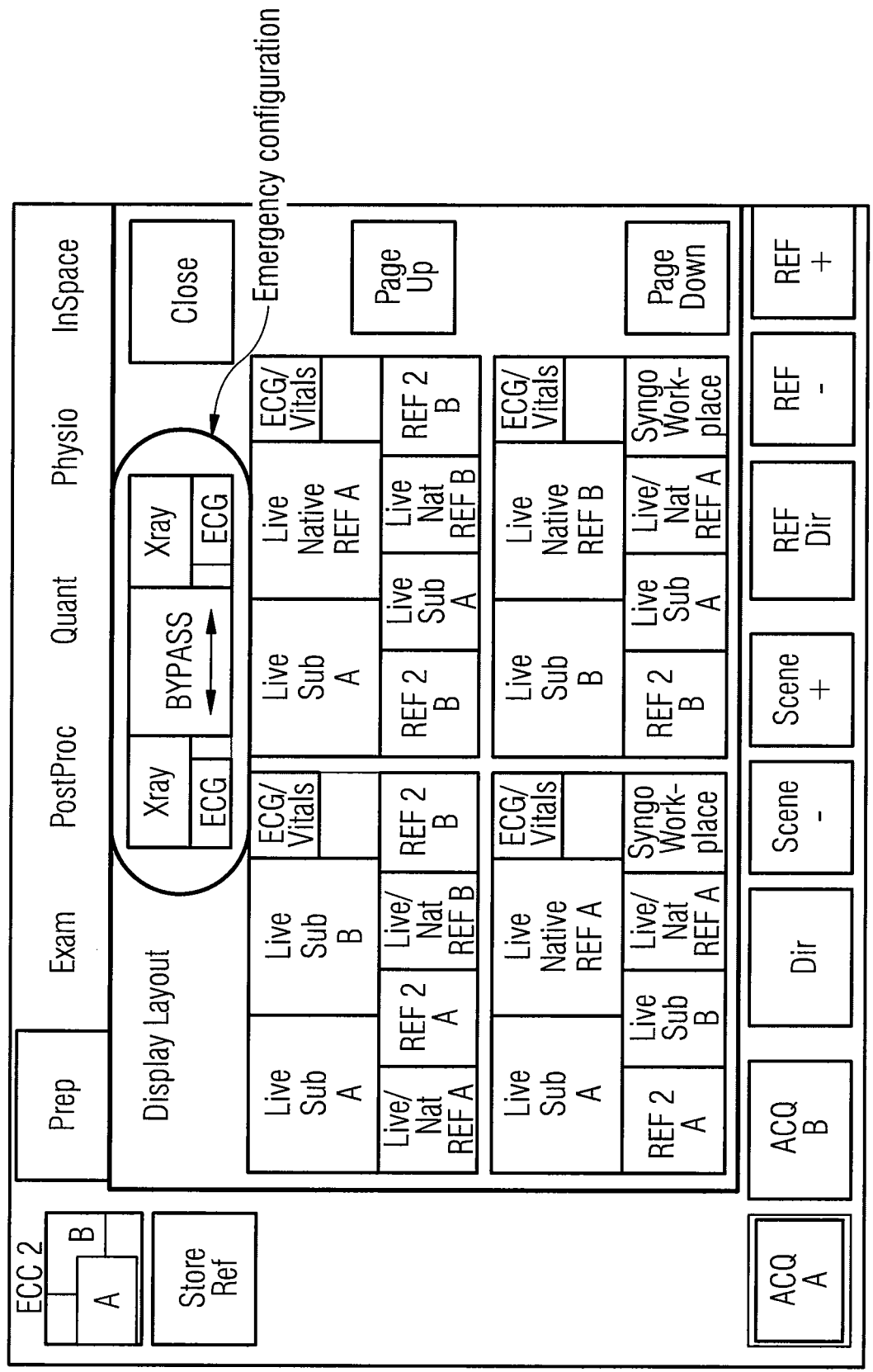
FIG. 4 shows a visual output of an input device with emergency configuration.

FIG. 4 shows an interface of an input system or operator console. A selection on the operator console may be used to select an image configuration. In FIG. 4, four image configurations are shown, the selected configuration being highlighted. The treating physician may select one of the image configurations, for example, by clicking or keying, which is then visually accentuated. An emergency configuration is also displayed. During normal operation the visual output serves to provide information for the operator, such as the treating physician. In the event of a failure, which adversely affects the output capability, the image configuration may be switched over to the emergency configuration, for example, manually.

FIG. 5 shows a system for representing image configurations on a large display 5. Image configurations for visual output on a large display 5 may be selected via an operator console 1, which is connected via a software control interface 2, to a medical system 3 and a graphics controller 4. The operator console 1 is used for operating or controlling the medical system 3. The medical system 3, is for example, an angiography facility by which angiography images are generated. The images are transferred to the graphics controller 4. In this case a plurality of inputs are provided in order that a plurality of images for visual output (e.g. reference images and difference images) can be transferred separately from the angiography facility to the graphics controller 4.

An image configuration is selected via the input device, such as the operator console 1. The image configuration is transferred to the graphics controller 4. The graphics controller 4 includes inputs to external video sources, for example, ECG, endoscopy, or ultrasound. The external video sources may be referenced by the image configuration, for example, for representation on the large display 5. The graphics controller 4 represents an adapting apparatus that composes (generates) an image in accordance with the selected image configuration and possibly other control information, and transfers a corresponding image signal to the large display 5.

In order to ensure that the total failure of a large display 5 used in medical technology applications does not restrict clinical operation, the system shown in FIG. 5 includes provision for an emergency operating mode.

For this purpose the large display 5 includes two halves, which are independent of each other and can be controlled separately. The large display 5 may include redundant power supplies for the electronics of the respective image halves and for the background illumination (backlight), such that if one power supply fails, the other continues to function in each case. If a power supply fails, a warning message is output on the display in order that service measures may be initiated.

If a power supply, the image backlight, or an image-half control unit fails, the large display 5 continues to represent half of the image. It is then possible to switch over to an emergency configuration by the operator console (FIG. 4 shows an interface of the operator console). The switchover is effected (e.g., triggered) by a selection. The emergency configuration may be defined (e.g. when the medical system 3 from FIG. 5 is installed) as follows: The user or the system configuration specifies which individual images are to be output in the event of a failure of one image half (emergency images: usually selected to allow continuation of the medical treatment procedure). If the left-hand image half fails, for example, the emergency images can be moved to the still functioning right-hand image half by selecting "Emergency configuration right" on the operator console (and vice versa).

While the invention has been described above by reference to various embodiments, it should be understood that many changes and modifications can be made without departing from the scope of the invention. For example, although the embodiments were discussed in conjunction with a particle therapy system, the same problems and solutions arise in photon therapy as well. It is therefore intended that the foregoing detailed description be regarded as illustrative rather than limiting, and that it be understood that it is the following claims, including all equivalents, that are intended to define the spirit and scope of this invention.

The invention claimed is:

1. A display for a representation of medical images, the display comprising:
    at least a first zone and a second zone that are controllable and operatable independently of each other,
    an image configuration that describes the representation on the display during a normal operating mode, and
    an emergency image configuration that describes the representation on the display during an emergency operating mode, wherein the display is operable to be switched from the normal operating mode to the emergency operating mode in the event of a failure or fault of the representation in the first zone or the second zone, wherein the emergency image configuration is selected to allow continuation of a medical treatment procedure associated with the image configuration, and wherein the emergency image configuration is selected by a user of the display.

2. The display as claimed in claim 1, wherein the first zone covers a first half of the display, and the second zone covers a second half of the display.

3. The display as claimed in claim 1, wherein the emergency image configuration provides for an output in the second zone of the display that is the same as an output in the first zone of the display when the display is in the normal operating mode.

4. The display as claimed in claim 1, further comprising an input device operable to allow the user to select the emergency image configuration prior to the failure or fault.

5. The display as claimed in claim 1, further comprising an input device operable to switch the display between the normal operating mode and the emergency operating mode.

6. The display as claimed in claim 1, wherein the emergency image configuration provides for an output in the second zone of the display that is different from an output in the first zone of the display when the display is in normal operating mode.

7. The display as claimed in claim 1, wherein:
the image configuration describes the representation on the first zone and the second zone during the normal operating mode,
the emergency image configuration describes the representation on the second zone during the emergency operating mode, and
the display is operable to be switched from the normal operating mode to the emergency operating mode when the representation in the first zone fails.

8. The display as claimed in claim 7, wherein the representation on the second zone during the emergency operating mode includes data that is not included in the representation on the first zone and the second zone during the normal operating mode.

9. A medical display system comprising:
a display, and
an adapting apparatus operable to generate an overall image in accordance with an image configuration for representation on the display when the medical display system is in a normal operating mode,
wherein the adapting apparatus is further operable to access an emergency image configuration for representation on the display when the medical display system is in an emergency operating mode and change the overall image for representation on the display in accordance with the emergency image configuration following a switchover of the medical display system from the normal operating mode to the emergency operating mode,
wherein the emergency image configuration is selected to allow continuation of a medical treatment procedure associated with the image configuration, and
wherein the emergency image configuration is selected by a user of the display.

10. The system as claimed in claim 9, further comprising an input unit operable to switch the medical display system to the emergency operating mode.

11. The system as claimed in claim 10, wherein the image configuration and the emergency image configuration are selected by the user via the input unit.

12. The system as claimed in claim 9, further comprising an input device operable to allow a user to manually switchover the medical display system from the normal operating mode to the emergency operating mode.

13. The system as claimed in claim 9, wherein the system is operable to allow for an automatic switchover of the medical display system from the normal operating mode to the emergency operating mode.

14. The system as claimed in claim 13, wherein the system is operable to automatically detect a fault in a zone of the display, wherein the fault is detected as a result of a verification message sent from the adapting apparatus to the display, or the fault is detected due to the absence of status reports that are regularly sent from the display to the adapting apparatus.

* * * * *